United States Patent [19]

van Loon

[11] Patent Number: Plant 6,490

[45] Date of Patent: Dec. 27, 1988

[54] CHRYSANTHEMUM PLANT NAMED CAPPA

[75] Inventor: Pieter L. van Loon, Sprang-Capelle, Netherlands

[73] Assignee: Hoek Breeding B.V., 's-Gravenzande, Netherlands

[21] Appl. No.: 39,063

[22] Filed: Apr. 16, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Cappa having anemone form, bright yellow ray florets and deeper yellow disc florets, a floriferous habit, and eight (8) week response.

1 Drawing Sheet

The present invention comprises a new and distinct cultivar of *Chrysanthemum morifolium,* Ramat., hereinafter referred to by the cultivar name Cappa.

Cappa is a product of a planned breeding program which had the objective of creating new Chrysanthemum cultivars with eight weeks flowering response, the ability to produce all year round, and improving the growth characteristics of the cultivar yellow Refour.

Cappa was originated by applicant from a hybridization made in a controlled breeding program in Sprang-Capelle, The Netherlands in 1980. The female parent was Refour, a white anemone centered cultivar. The male parent of Cappa was No. 70 unnamed seedling), a deep yellow anemone centered variety. Cappa was discovered and selected as one flowering plant within the progeny of the stated parentage by applicant Pieter L. van Loon on Oct. 29, 1981 in a controlled environment in Sprang-Capelle, The Netherlands.

The first act of asexual reproduction of Cappa was accomplished when vegetative cuttings were taken from the initial selection on Jan. 4, 1982 in a controlled environment in Sprang-Capelle, The Netherlands by a technician working under formulations established and supervised by applicant. Horticultural examination of selected units initiated July 10, 1982 has demonstrated that the combination of characteristics as herein disclosed for Cappa are firmly fixed and are retained through successive generations of asexual reproduction.

Cappa has not been observed under all possible environmental conditions. The phenotype may vary significantly with variations in environment such as temperature, light intensity, and day length. The following observations, measurements and comparisons describe plants grown in Sprang-Capelle, The Netherlands under greenhouse conditions which approximate those generally used in commercial practice.

Of the many commercial cultivars known to the present inventor, the most similar in comparison to Cappa is Yellow Refour. Reference is made to attached Chart A which compares certain characteristics of Cappa to those same characteristics of Yellow Refour. In comparison to Yellow Refour, Cappa has less tendency to discolor its ray florets under high finishing temperatures; produces more ray florets; has shorter peduncles, and its leaves have a less intense green color. The capitulum form and type of Cappa are similar to those same characteristics of Yellow Refour.

The accompanying photographic drawing shows typical inflorescence and foliage characteristics of Cappa, with colors being as nearly true as possible with illustrations of this type.

In the following description, color references are made to The Royal Horticultural Society Colour Chart. The color values were determined between noon and 1:00 p.m. on July 10, 1982 under 30 foot candle light intensity at Sprang-Capelle, The Netherlands.

Classification:

*Botanical.*—*Chrysanthemum morifolium,* Ramat., cv Cappa.

*Commercial.*—Cut spray, anemone-type.

INFLORESCENCE

A. Capitulum:

*Form.*—Corymbiform.

*Type.*—Semi-double.

*Diameter across face.*—50 mm.

B. Corolla of ray florets:

*Color (general tonality from a distance of three meters).*—Yellow.

*Color (upper surface).*—Yellow 5C, fading to approximately 2D.

*Color (under surface).*—Yellow 6D.

C. Corolla of disc florets:

*Color (mature).*—Yellow 12A.

*Color (immature).*—Yellow 9A.

PLANT

A. General appearance:

*Height.*—Medium.

B. Foliage:

*Color (upper surface).*—Yellow green 147A.

*Shape.*—Base cordate, margins pinnately lobed, with deep indentations, apex mucronate.

CHART A

COMPARISON OF CAPPA AND YELLOW REFOUR

| CULTIVAR | RAY FLORET COLOR | CAPITULUM FORM AND TYPE | POLLEN PRODUCTION |
|---|---|---|---|
| CAPPA | yellow RHS 6D | semi-double anemone-centered | none |
| YELLOW REFOUR | yellow RHS 8D | semi-double anemone-centered | sparse |
| | DIAMETER | | |

CHART A-continued

COMPARISON OF CAPPA AND YELLOW REFOUR

| CULTIVAR | ACROSS FACE OF CAPITULUM | PLANT HEIGHT | FLOWERING RESPONSE PERIOD |
|---|---|---|---|
| CAPPA | 50 to 60 mm | medium | 8 weeks |

CHART A-continued

COMPARISON OF CAPPA AND YELLOW REFOUR

| | | | |
|---|---|---|---|
| YELLOW REFOUR | 45 to 55 mm | short to medium | 8 weeks |

I claim:

1. A new and distinct Chrysanthemum plant named Cappa, as illustrated and described, and parts thereof.

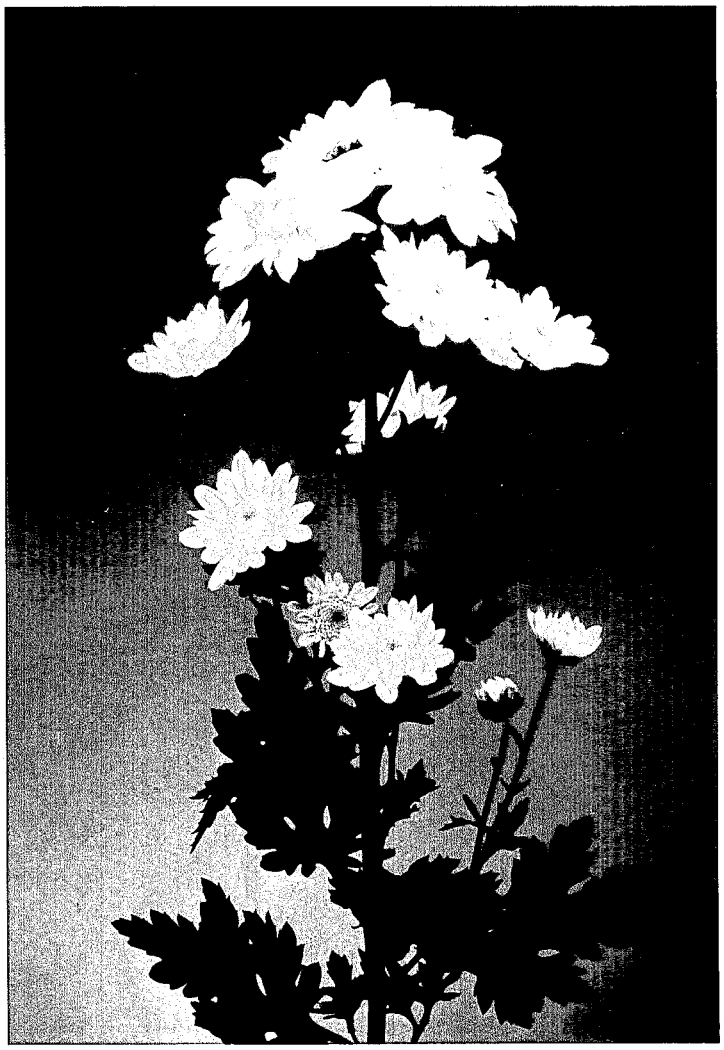

* * * * *